US012551377B2

(12) United States Patent
Rathjen et al.

(10) Patent No.: US 12,551,377 B2
(45) Date of Patent: Feb. 17, 2026

(54) DEVICE FOR TREATING EYE TISSUE BY MEANS OF A PULSED LASER BEAM

(71) Applicant: Ziemer Ophthalmic Systems AG, Port (CH)

(72) Inventors: Christian Rathjen, Bremen (DE); Michael Steinlechner, Zurich (CH)

(73) Assignee: Ziemer Ophthalmic Systems AG, Port (CH)

( * ) Notice: Subject to any disclaimer, the term of this patent is extended or adjusted under 35 U.S.C. 154(b) by 1072 days.

(21) Appl. No.: 17/358,229

(22) Filed: Jun. 25, 2021

(65) Prior Publication Data

US 2021/0401622 A1 Dec. 30, 2021

(30) Foreign Application Priority Data

Jun. 25, 2020 (CH) .................................... 00770/20

(51) Int. Cl.
*A61F 9/008* (2006.01)

(52) U.S. Cl.
CPC .... *A61F 9/008* (2013.01); *A61F 2009/00872* (2013.01); *A61F 2009/00897* (2013.01)

(58) Field of Classification Search
CPC .. A61F 9/008; A61F 9/00827; A61F 9/00829; A61F 2009/00844; A61F 2009/00851; A61F 2009/00872; A61F 2009/00897; A61F 9/009
USPC .............................................................. 606/5
See application file for complete search history.

(56) References Cited

U.S. PATENT DOCUMENTS

| | | | | |
|---|---|---|---|---|
| 7,621,637 | B2 | 11/2009 | Rathjen et al. | |
| 10,918,523 | B2 | 2/2021 | Rathjen | |
| 2007/0237620 | A1 | 10/2007 | Muhlhoff et al. | |
| 2011/0205492 | A1* | 8/2011 | Rathjen | A61B 3/0008 351/221 |
| 2016/0089270 | A1* | 3/2016 | Fu | A61F 9/00827 606/5 |
| 2018/0028355 | A1* | 2/2018 | Raksi | A61B 3/13 |

(Continued)

FOREIGN PATENT DOCUMENTS

| | | | |
|---|---|---|---|
| DE | 102006053117 | A1 | 5/2008 |
| EP | 3427705 | A1 | 1/2019 |
| WO | 2005048895 | A1 | 6/2005 |

OTHER PUBLICATIONS

Sep. 22, 2020—(CH) Search Report—App 7702020.

*Primary Examiner* — Ahmed M Farah
(74) *Attorney, Agent, or Firm* — Banner & Witcoff, Ltd.

(57) ABSTRACT

An ophthalmological device comprises a laser source, an application head having focusing optics and a patient interface, a scanner system and circuit. The circuit is configured to control the scanner system to incise an incision surface, which is symmetrical with respect to the central axis of the patient interface, in the eye tissue, a pulsed laser beam being steered onto treatment points on the incision surface on a first treatment path, and the treatment path being curved while extending around the projection axis of the focusing optics. In the event of a tilt of the eye with respect to the central axis of the patient interface, the circuit determines an apex of a tilted incision surface by a co-tilt of the incision surface corresponding to the tilt of the eye, and determines a transformed treatment path, which extends around the apex and determines treatment points on the tilted incision surface.

17 Claims, 6 Drawing Sheets

(56) References Cited

U.S. PATENT DOCUMENTS

| | | | | |
|---|---|---|---|---|
| 2020/0330268 | A1* | 10/2020 | Rathjen | A61F 9/008 |
| 2021/0128360 | A1* | 5/2021 | Thorlakson | A61F 9/00825 |
| 2021/0401622 | A1* | 12/2021 | Rathjen | A61F 9/008 |

* cited by examiner

DEVICE FOR TREATING EYE TISSUE BY MEANS OF A PULSED LASER BEAM

CROSS-REFERENCE TO RELATED APPLICATION

The present application claims priority to and the benefit of Switzerland Patent Application 00770/20 filed Jun. 25, 2020, which is incorporated by reference in its entirety herein.

FIELD OF DISCLOSURE

The present disclosure relates to an ophthalmological device for treating eye tissue by means of a pulsed laser beam. The present disclosure relates in particular to an ophthalmological device having a laser source for generating a pulsed laser beam, focusing optics for focusing the pulsed laser beam into the eye tissue, and a scanner system in order to steer the pulsed laser beam onto treatment points on a treatment path.

BACKGROUND OF THE DISCLOSURE

In order to treat eye tissue by means of a laser beam, a treatment region is scanned with a focused laser beam, by the generally pulsed laser beam being deflected by means of suitable scanner systems (deflecting devices) in one or two scan directions. The deflection of the light beams, or of the laser pulses, for example femtosecond laser pulses, is generally carried out with movable mirrors that can be pivoted about one or two scan axes, for example with galvanoscanners, piezoscanners, polygon scanners or resonant scanners.

In order to generate incision surfaces, tissue regions, which are separated by individual laser pulses, are placed so close together that an uninterrupted separated tissue region is formed. In order to generate curved or arbitrarily oriented incision surfaces, it is furthermore necessary to adjust the focus of the laser beam in the beam direction by means of divergence-modulating means (for example movable lenses) or focusing optics with movement drivers. WO2005/048895 describes, for example, a system having a mirror deflection system and a focusing device.

As an alternative to scanning with galvanoscanners, U.S. Pat. No. 7,621,637 describes a device for treating eye tissue which comprises a base station having a laser source for generating laser pulses and a scanner, arranged in the base station, having movable deflecting mirrors for deflecting the laser pulses in a scan direction. The deflected laser pulses are transmitted by means of an optical transmission system from the base station to an application head, which tracks along a working region according to a scan pattern by means of mechanically moved projection optics. The deflection in the scan direction, which is much faster compared with the mechanical movement, is superimposed in the application head on the mechanical movement of the projection optics and therefore on the scan pattern of the head. A fast scanner system in the base station allows fine movement of the laser pulses (microscan), which is superimposed on the scan pattern of the movable projection optics, which covers a large treatment range, for example the entire eye.

US 2016/0089270 describes a system and a method for incising lenticules in eye tissue. According to US 2016/0089270, to this end rectilinear fast scan lines are superimposed on slower treatment lines, which are moved along meridians of the lenticule. By the rectilinearity of the fast scan lines, incisions are formed which deviate in their shape from the desired surface curvature of the lenticule and therefore cause errors. Furthermore, in order to track the treatment lines along the meridians respectively through a distance of a lenticule width, a vertical focus displacement of the order and extent of the thickness of the lenticule to be incised is necessary, which is associated on the one hand with corresponding outlay and costs for the displaceable optics and movable lenses configured therefor and on the other hand with concomitant reductions in the treatment speed. Furthermore, because of their fixed horizontal alignment, the fast scan lines do not allow optimal adaptation of incisions to lenticule surfaces, particularly not when the latter deviate from a spherical shape.

EP3427705 describes an ophthalmological device for treating eye tissue by means of a pulsed laser beam, which comprises a scanner system that is configured to steer the pulsed laser beam onto treatment target points along a fast scan line extending transversely at an alignment angle with respect to a treatment line, and to tilt the fast scan line as a function of the treatment target point to the treatment line in such a way that the fast scan line extends substantially along an outer surface of a lenticule to be incised in the eye tissue.

Such known systems do allow the treatment of simple scan patterns, for example the incision of a tissue flap, which is generally formed as a large flat portion with a simple edge geometry. In applications in which tissue incisions in a substantially horizontally aligned treatment surface are not only intended to be carried out on an entire focal surface, but in which incisions with a vertical incision component are also intended to be carried out over different focal heights, for example incisions extending obliquely with respect to the horizontal or vertical incisions, the vertical movement of the projection optics or of a zoom system for a vertical modification of the focus, and therefore the incision height, proves too slow for carrying out incisions with a vertical component, i.e. with a variable focal depth during the incision, with a speed that is comparable with incision speeds in the horizontal treatment surface.

In order to achieve short treatment times, for a given incision geometry, ways of guiding incisions that minimize the required movement speeds in the vertical direction are sought. For example, the incision of a spherical cap is carried out by means of a spiral with a monotonically increasing or decreasing focal depth without alternating displacement movements.

DE102006053117 describes a device for operative visual defect correction of a patient's eye, which separates corneal tissue by means of pulsed laser radiation. In this case, the laser radiation is focused onto target points that lie on a pattern in the cornea. The focused laser radiation is guided along a path over the pattern of the target points, and laser pulses are also delivered in the cornea onto points that lie on the path between the target points.

In the ophthalmological devices mentioned above for treating eye tissue by means of pulsed laser beams, the eyes to be treated are fixed in relation to the ophthalmological devices. In general, to this end a patient interface, which is fixed on the eye by means of reduced pressure, is used. For the treatment of the eye tissue, the patient interface is connected securely or removably to the ophthalmological device. The fixing of the eye to be treated in relation to the ophthalmological device makes it possible that the scanner system can generate an incision surface to be incised in the eye tissue by executing a defined (programmed) incision pattern, without thereby being impaired by eye movements. However, tilts of the eye in relation to the patient interface, for example in the event of tilted application of the patient interface on the eye, or vice versa, proves problematic in this case since incision surfaces in the eye tissue, made according to the defined incision pattern, are therefore not incised at the intended place.

In the case of a curved patient interface, for example, a new focal depth profile must be imposed on the originally defined scan pattern. In the case of incising a spherical cap along a spiral, this results in focus adjustment movements that have a further alternating component besides a monotonically increasing or decreasing component. This alternating component alternates with the revolution frequency of the spiral and leads to changes in the focus adjustment speed during a revolution, the amplitude of the adjustment depending on the degree of the tilt. Focus adjustment drives can carry out this speed change only up to their inherent performance limits. If the requirements extend beyond this, the execution speed of the entire system must be reduced to such an extent that the focus adjustment drives can again follow the focal depth profile. An associated slowing of the treatment and increase of the treatment time is often undesirable for various reasons.

SUMMARY OF THE DISCLOSURE

It is an object of the present disclosure to propose an ophthalmological device for treating eye tissue by means of a pulsed laser beam, which does not have at least some disadvantages of the prior art. It is in particular an object of the present disclosure to propose an ophthalmological device for treating eye tissue by means of a pulsed laser beam, which makes it possible to incise incision surfaces at the intended place in the eye tissue even in the event of a tilt of the eye in relation to the patient interface.

According to the present disclosure, these objects are achieved by the features of the independent claim. Further advantageous embodiments may also be found from the dependent claims and the description.

An ophthalmological device for treating eye tissue of an eye comprises a laser source, which is configured to generate a pulsed laser beam, and an application head having focusing optics and a patient interface. The focusing optics have a projection axis and are configured to focus the pulsed laser beam in the eye tissue onto a treatment point. The patient interface has a central axis and is configured to fix the application head on the eye. The ophthalmological device also comprises a scanner system, which is configured to steer the pulsed laser beam in the eye tissue onto treatment points on a treatment path. The ophthalmological device furthermore comprises a circuit, which is configured to control the scanner system in order to incise an incision surface, which is symmetrical with respect to the central axis of the patient interface, in the eye tissue, the pulsed laser beam being steered onto treatment points on the incision surface on a first treatment path, and the first treatment path being curved while extending around the projection axis of the focusing optics.

The objects mentioned above are achieved in that the circuit is furthermore configured, in the event of a tilt of the eye with respect to the central axis of the patient interface, to determine an apex of a tilted incision surface, which is determined by a co-tilt of the incision surface corresponding to the tilt of the eye, to determine a transformed second curved treatment path, which extends around the apex of the tilted incision surface and determines treatment points on the tilted incision surface, and to control the scanner system in such a way that the pulsed laser beam is steered onto treatment points on the transformed second curved treatment path.

In an embodiment, the focusing optics are configured to adjust a treatment height of the treatment points in the direction of the projection axis with a focus adjustment speed, the scanner system is configured to displace treatment points on the treatment path with a scan speed that is higher than the focus adjustment speed, and the circuit is configured to determine the transformed second curved treatment path with height changes in the direction of the projection axis which are adjustable during a movement of treatment points with the scan speed without exceeding the focus adjustment speed of the focusing optics.

In an embodiment, the first treatment path has a continual height change component in the direction of the projection axis, and the circuit is configured to determine the transformed second curved treatment path with a treatment height component increasing continually or decreasing continually in the direction of the projection axis.

In an embodiment, the first treatment path has a continual height change component in the direction of the projection axis, and the circuit is configured to determine subsections of the transformed second curved treatment path with a path section treatment height that is respectively constant in the direction of the projection axis, and to prevent generation of the pulsed laser beam by the laser source while the focusing optics are adjusting the path section treatment height of two subsections, adjacent in the direction of the projection axis, of the transformed second curved treatment path.

In an embodiment, subsections of the first treatment path respectively have a path section treatment height that is constant in the direction of the projection axis, and the circuit is configured to determine the transformed second curved treatment path with a treatment height component increasing continually or decreasing continually in the direction of the projection axis.

In an embodiment, subsections of the first treatment path respectively have a path section treatment height that is constant in the direction of the projection axis, and the circuit is configured to determine subsections of the transformed second curved treatment path with a path section treatment height that is respectively constant in the direction of the projection axis, and to prevent generation of the pulsed laser beam by the laser source while the focusing optics are adjusting the path section treatment height of two subsections, adjacent in the direction of the projection axis, of the transformed second curved treatment path.

In an embodiment, the circuit is configured to determine the transformed second curved treatment path with a treatment height component alternately increasing and decreasing in the direction of the projection axis.

In an embodiment, the first treatment path comprises path sections having at least one of the following shapes: a circular path section, an elliptical path section, a parabolic path section, a hyperbolic path section, a helical path section, or a spline path section.

In an embodiment, the circuit is configured to determine the transformed second curved treatment path on the basis of the first curved treatment path by carrying out at least one of the following operations: stretching first regions of the first curved treatment path, compressing second regions of the first curved treatment path, and/or interrupting third regions of the first curved treatment path.

In an embodiment, the circuit is configured to control the scanner system in order to incise a lenticule, which is formed by two incision surfaces and is symmetrical with respect to the central axis of the patient interface in the eye tissue, and in the event of a tilt of the eye with respect to the central axis of the patient interface, to determine an apex of a tilted lenticule which is determined by a co-tilt of the lenticule corresponding to the tilt of the eye, to determine transformed third curved treatment paths which extend around the apex and determine treatment points on the incision surfaces of the tilted lenticule, and to control the scanner system in such a way that the pulsed laser beam is steered onto treatment points on the transformed third curved treatment paths.

In an embodiment, the patient interface comprises a curved internal space, which is symmetrical with respect to the central axis, for receiving a corneal region of the eye.

In an embodiment, the patient interface comprises a planar internal space, which is symmetrical with respect to the central axis, for receiving a corneal region of the eye.

In an embodiment, the ophthalmological device comprises a measuring device which is configured to register reference structures and/or reference markings in or on the eye tissue, and the circuit is configured to determine the tilt of the eye with respect to the central axis of the patient interface on the basis of the reference structures and/or reference markings registered by the measuring device.

In an embodiment, the circuit is configured to determine the tilt of the eye with respect to the central axis of the patient interface by determining a displacement of the corneal region of the eye in relation to a contact surface of the curved internal space of the patient interface.

In an embodiment, the ophthalmological device comprises one or more suction elements, which are configured to fix the patient interface on the eye.

In an embodiment, the scanner system comprises a first scan device, which is configured to steer the pulsed laser beam in the eye tissue with a feed speed along a feed line on the treatment path, and the scanner system comprises a second scan device, which is configured to steer the pulsed laser beam in the eye tissue with a scan speed, which is higher than the feed speed, along a scan line extending transversely with respect to the feed line on the treatment path.

BRIEF DESCRIPTION OF THE DRAWINGS

An embodiment of the present disclosure will be explained below with the aid of an example. The embodiment example is illustrated by the following appended figures.

DESCRIPTION OF THE EMBODIMENTS

Figure 1:
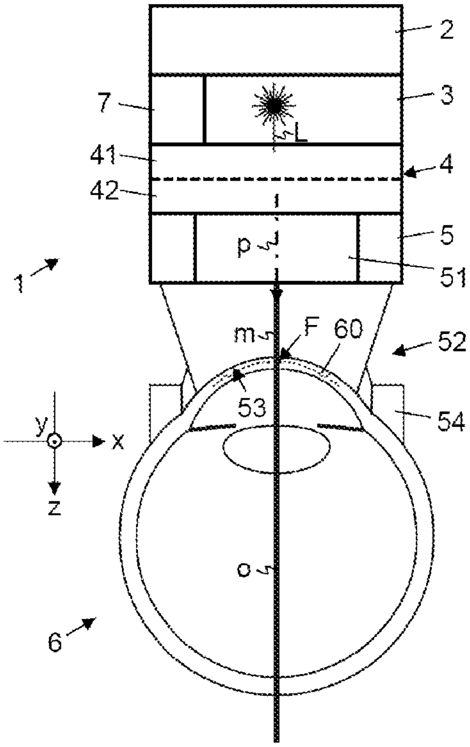
FIG. 1 shows a block diagram, which schematically illustrates an ophthalmological device for treating eye tissue with a pulsed laser beam, which is fixed on the eye by means of a patient interface.
Figure 2:
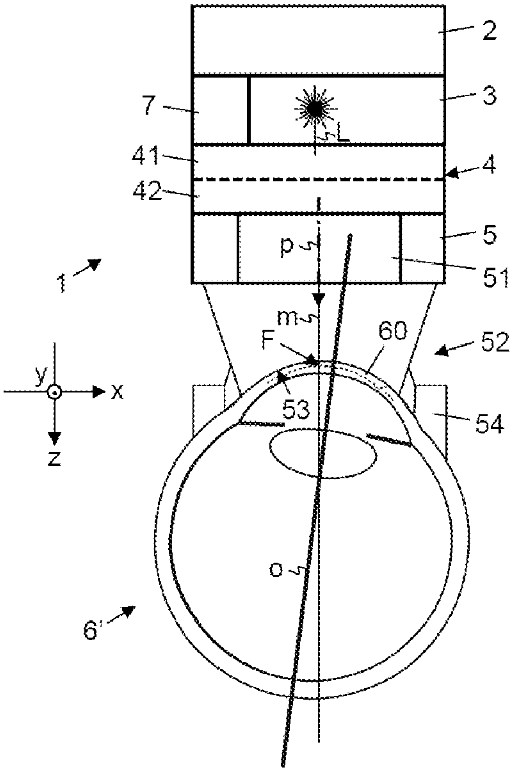
FIG. 2 shows a block diagram, which schematically illustrates an ophthalmological device for treating eye tissue with a pulsed laser beam, which is fixed on the eye by means of a patient interface, the eye being tilted with respect to the central axis of the patient interface.

In FIGS. 1 and 2, the reference 1 respectively refers to an ophthalmological device for treating eye tissue 60 by means of laser pulses, for example the cornea or another tissue of an eye 6.

As is schematically represented in FIGS. 1 and 2, the ophthalmological device 1 comprises a laser source 3, a scanner system 4, and an application head 5 having focusing optics 51 and a patient interface 52.

The laser source 3 is configured to generate a pulsed laser beam L. The laser source 3 comprises in particular a femtosecond laser for generating femtosecond laser pulses, which have pulse widths of typically from 10 fs to 1000 fs (1 fs=$10^{-15}$ s). The laser source 3 is arranged in a separate housing or a common housing with the focusing optics 51.

The scanner system 4 is configured to steer the pulsed laser beam L delivered by the laser source 3 by means of the focusing optics 51 in the eye tissue 60 onto treatment points F on a treatment path t, t' (trajectories t and t'). As is schematically represented in FIGS. 1 and 2, the scanner system 4 comprises a plurality of scan devices: a first scan device 41 (fast scan module) and a second scan device 42 (slow scan module). In an embodiment, the scanner system 4 comprises a divergence modulator for modulating the focal depth, or the treatment height, in the projection direction along the projection axis p.

The scan device 42 (slow scan module) placed in front of the focusing optics 51 is configured to steer the pulsed laser beam L, or its laser pulses, in the eye tissue 60 in an x/y treatment plane with a feed speed (a speed of advance) along a feed line (a line of advance) on the treatment path t, t', as is illustrated for example in FIGS. 5, 6, 7, 8 and 10. The scan device 42 is configured as a mechanical scanner, which tracks the focusing optics 51 over a treatment zone along the treatment path t, t' by means of one or more movement drivers, so that the focus of the focusing optics 51 is guided in the x/y treatment plane along the treatment path t, t', or the scan device 42 is configured to be beam-deflecting and comprises one or two deflecting mirrors respectively movable about one or two axes for deflecting the pulsed laser beam L, or the laser pulses, in the x/y treatment plane along the treatment path t, t'. The beam-deflecting scan device 42 is configured as a freely addressable scanner and comprises, for example, a galvanoscanner or a piezo-driven scanner.

In an embodiment, the scan device 41 (as a fast scan module) preceding the scan device 42 is configured to steer the pulsed laser beam L, or its laser pulses, in the eye tissue 60 in the x/y treatment plane with a scan speed that is higher in relation to the feed speed along a scan line extending transversely with respect to the feed line. The two scan devices 41 and 42 are configured and coupled in such a way that the scan movement, extending along the scan line, of the scan device 41 is superimposed on the feed line of the scan device 42. The scan device 41 comprises one or more movable deflecting mirrors, for example a rotating polygonal mirror (polygon scanner), one or more resonant mirrors (resonant scanner) or oscillating mirrors (oscillating scanner), which are for example piezo-driven (piezo scanner), or MEM (Micro-ElectroMechanical) scanner, or the scan device 41 comprises an AOM (Acousto-Optical Modulator) scanner or an EOM (Electro-Optical Modulator) scanner. The scan device 41 has a scan speed that is higher, for example several times, than the subsequent scan device 42 (feed speed). In order to avoid misunderstandings, it should be mentioned at this point that in the embodiment in which the scan device 41 configured as a fast scan module generates scan lines that extend transversely with respect to the feed line of the scan device 42, the feed line of the subsequent scan device 42 corresponds to the treatment path t, t', the transversely extending scan lines of the scan device 41 placed in front treating intermediate spaces between the treatment path t, t'.

As is schematically represented in FIGS. 1, 2 and 4-7, the application head 5 comprises focusing optics 51 and a patient interface 52. The application head 5 can be placed onto the eye 6 and fixed on the eye 6 by means of the patient interface 52. For the sake of simplicity, only the application head 5 applied and fixed on the eye 6 is respectively represented in FIGS. 4-7, without reproducing the further modules of the ophthalmological device 1, which are represented in FIGS. 1 and 2.

For the treatment and incision of incision surfaces C, C' which have a lateral component in the x/y treatment plane normal to the projection direction which is comparatively larger than the depth component in the projection direction along the projection axis p, the scanner system 4 is configured to displace the treatment points F, onto which the laser pulses are focused, with a higher scan speed on the treatment path t, t' in relation to the focus adjustment speed of the focusing optics 51.

Figure 3:
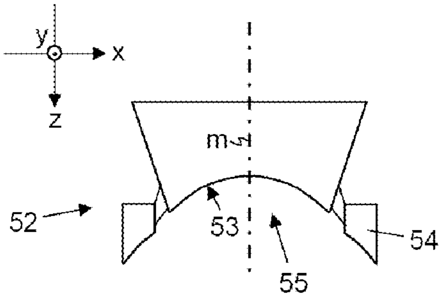
FIG. 3 shows a schematic cross-sectional view of a patient interface of the ophthalmological device with a curved internal space for receiving a corneal region of the eye and suction elements for fixing the patient interface on the eye.

As is schematically represented in FIGS. 1 to 7, the patient interface 52 comprises one or more holding elements, for example suction elements 54, for fixing the patient interface 52 on the eye 6. The suction element 54 is, for example, configured as a suction ring. As is schematically represented in FIG. 3, the patient interface 52 comprises a curved internal space 55 for receiving a corneal region of the eye 6. The curved internal space 55 is symmetrical with respect to the central axis m of the patient interface 52. The curved internal space 55 is formed by a contact surface 53 of the patient interface 52. In the applied state, the contact surface 53 of the patient interface 52 makes contact with the outer surface of the cornea 60 of the eye 6. Depending on the embodiment, the patient interface 52 is connected securely or removably to the focussing optics 51.

As is schematically represented in FIGS. 1 and 2, the ophthalmological device 1 comprises a circuit 2 for controlling the laser source 3, the optical functional module of the scanner system 4, the focusing optics 51, and the measuring device 7 described below. The circuit 2 embodies a programmable control device and comprises, for example, one or more processors having program and data memories as well as programmed software modules for controlling the processors, and/or other programmable circuits or logic units such as ASICs (Application-Specific Integrated Circuits).

As is schematically represented in FIGS. 1 and 2, the ophthalmological device 1 comprises a measuring device 7, for example an imaging measuring device, for example a video sensor, or an interferometric measuring device, for example an OCT (Optical Coherence Tomography) system, which is optically coupled into the beam path of the scanner system 4 towards the focussing optics 51. The measuring device 7 is configured to register reference structures and/or reference markings in or on the eye tissue 60 via the beam path. The measuring device 7 is connected to the circuit 2. The circuit 2 is configured, on the basis of the reference structures and/or reference markings registered by the measuring device 7, to detect tilts of the eye 6 in relation to the patient interface 52, in particular tilts of the eye 6 in relation to the central axis m of the patient interface 52. In an embodiment, the circuit 2 is configured to determine the tilts of the eye 6 in relation to the patient interface 52 by determining displacements of the corneal region of the eye 6, or of the determined reference structures and/or reference markings, in relation to the contact surface 53 in the curved internal space of the patient interface 52.

Figure 4:
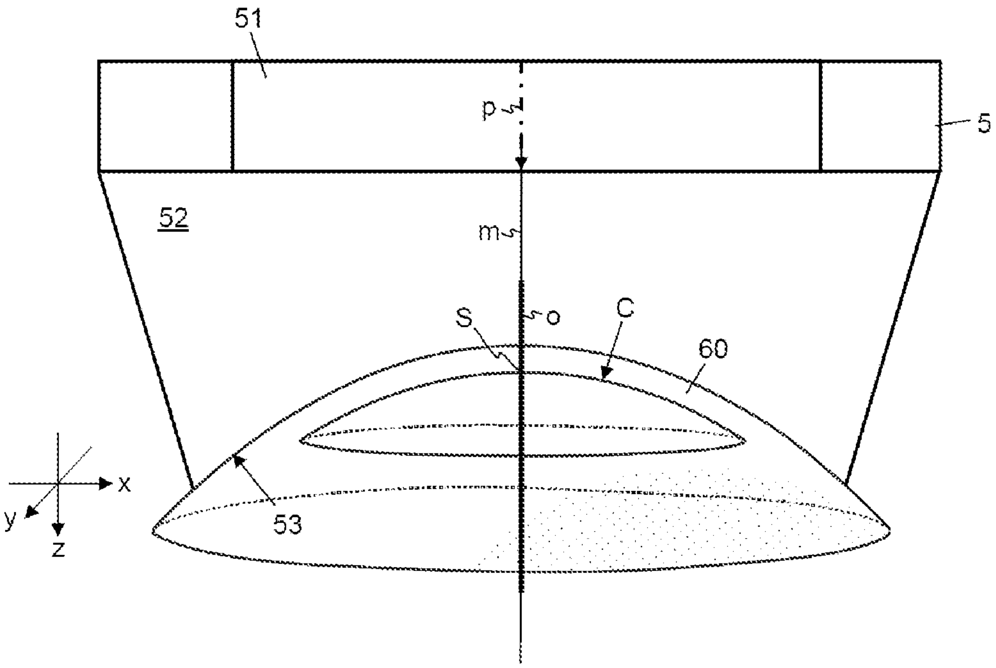
FIG. 4 shows a schematic cross-sectional view of an incision surface in an eye tissue region which is adjacent to a contact surface of the patient interface and is arranged untilted with respect to the central axis of the patient interface in the curved internal space of the patient interface
Figure 6:
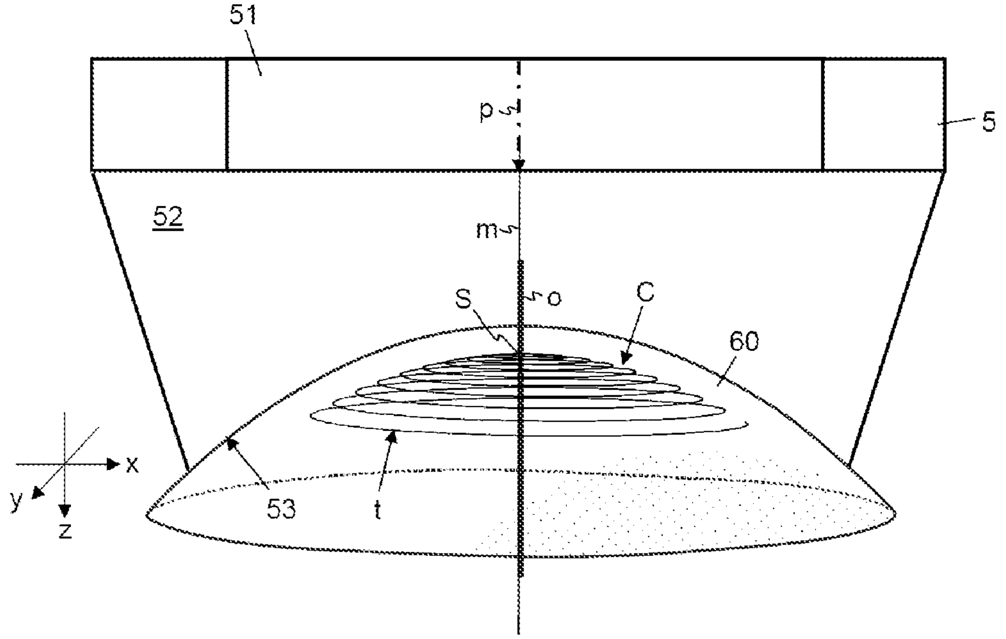
FIG. 6 shows a schematic cross-sectional view of a curved treatment path, extending around the projection axis of focusing optics, for incising an incision surface in an eye tissue region which is adjacent to a contact surface of the patient interface and is arranged untilted with respect to the central axis of the patient interface in the curved internal space of the patient interface.

FIGS. 1, 4 and 6 represent situations in which the eye 6 is aligned coaxially with respect to the central axis m of the patient interface 52. In other words, the eye axis o extending through the apex of the eye 6 extends substantially coaxially with respect to the central axis m of the patient interface 52. In the case of an ideal arrangement and alignment of the patient interface 52 with respect to the focusing optics 51, the central axis m of the patient interface 52 extends coaxially with respect to the projection axis p of the focusing optics 51.

FIGS. 4 and 6 represent incision surfaces C in the eye tissue 60, particularly in the cornea of the eye 6, which are symmetrical with respect to the central axis m of the patient interface 52 when the central axis m of the patient interface 52 is aligned coaxially with respect to the projection axis p of the focusing optics 51. In the case of coaxial alignment of the eye 6 with respect to the central axis m of the patient interface 5, the incision surfaces C are also coaxial with respect to the eye axis o in the eye tissue 60, which extends through the apex of the eye 6. In an embodiment, the incision surface C comprises two partial incision surfaces, which determine, or form, a lenticule in the eye tissue 60, which is symmetrical with respect to the central axis m of the patient interface 52. In the following embodiments relating to the incision surface C and a tilted incision surface C', this formation of the lenticule by the partial incision surfaces of the incision surface C, or by the partial incision surfaces of the tilted incision surface C', are always to be understood even if this is not discussed further.

A treatment path t for incising the incision surface C is illustrated in the example of FIG. 6. The treatment path t for incising the incision surface C is curved and extends around the projection axis p of the focusing optics 51. In the example of FIG. 6, the treatment path t is a helical path which extends on the incision surface C starting from the apex S of the incision surface C and has a continual slope with a monotonic change in the treatment height in the direction of the projection axis p. In this case, the apex S of the incision surface C is the highest point of the incision surface C in respect of the direction of the projection axis p. The treatment path t furthermore has a distance from the projection axis p that becomes greater with a decreasing treatment height, or increasing treatment depth. The person skilled in the art will understand that the incision process by scanning the treatment path t may be carried out starting from its deepest point in the eye 6 towards its apex S, or vice versa. Depending on the embodiment and configuration, the treatment path t comprises one or more mutually separated or connected path sections. The path sections have a circular, elliptical, parabolic, hyperbolic, helical and/or spline shape. The treatment path t for incising an incision surface C is defined by stored control data. On the basis of the control data, the circuit 2 controls the laser source 3, the scanner system 4 and/or the focusing device 51 in order to incise the incision surface defined by the control data by scanning the treatment path t by means of the pulsed laser beam L.

Figure 5:
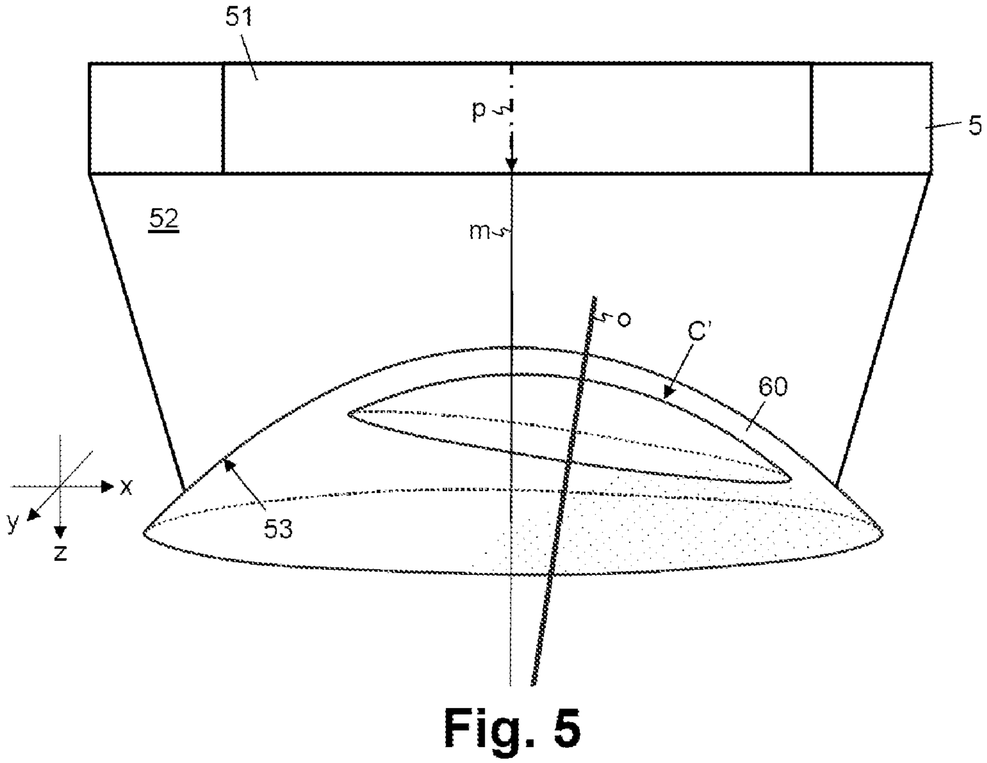
FIG. 5 shows a schematic cross-sectional view of an incision surface in an eye tissue region which is adjacent to a contact surface of the patient interface and is arranged tilted with respect to the central axis of the patient interface in the curved internal space of the patient interface.
Figure 7:
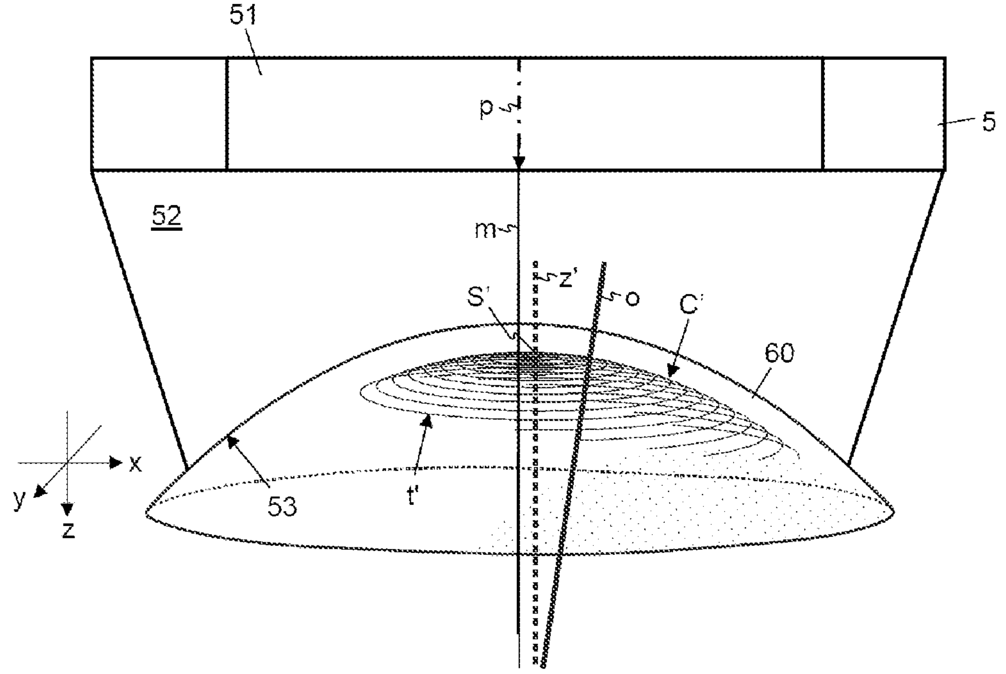
FIG. 7 shows a schematic cross-sectional view of a curved treatment path, extending around a displaced apex of a tilted incision surface, with interruptions for incising an incision surface in an eye tissue region which is adjacent to a contact surface of the patient interface and is arranged tilted with respect to the central axis of the patient interface in the curved internal space of the patient interface.

FIGS. 2, 5 and 7 represent situations in which the eye 6 is tilted with respect to the central axis m of the patient interface 52. In other words, the eye axis o extending through the apex of the eye 6 extends obliquely or transversely with respect to the central axis m of the patient interface 52. In the case of tilted arrangement and alignment of the eye 6 with respect to the patient interface 52, the eye 6 is also correspondingly tilted with respect to the projection axis p of the focussing optics 51. FIGS. 5 and 7 represent tilted incision surfaces C' in the eye tissue 60, which are co-tilted with the tilt of the eye 6 and are therefore symmetrical with respect to the eye axis o. Because of the curved internal space 55, or the correspondingly curved contact surface 53 of the patient interface 52 which makes contact with the cornea of the eye 6 when the patient interface 52 is applied, a tilt of the eye 6 with respect to the central axis m of the patient interface 52 corresponds substantially to a displacement of the outer surface of the cornea with respect to the contact surface 53 of the patient interface 52.

Figure 12:
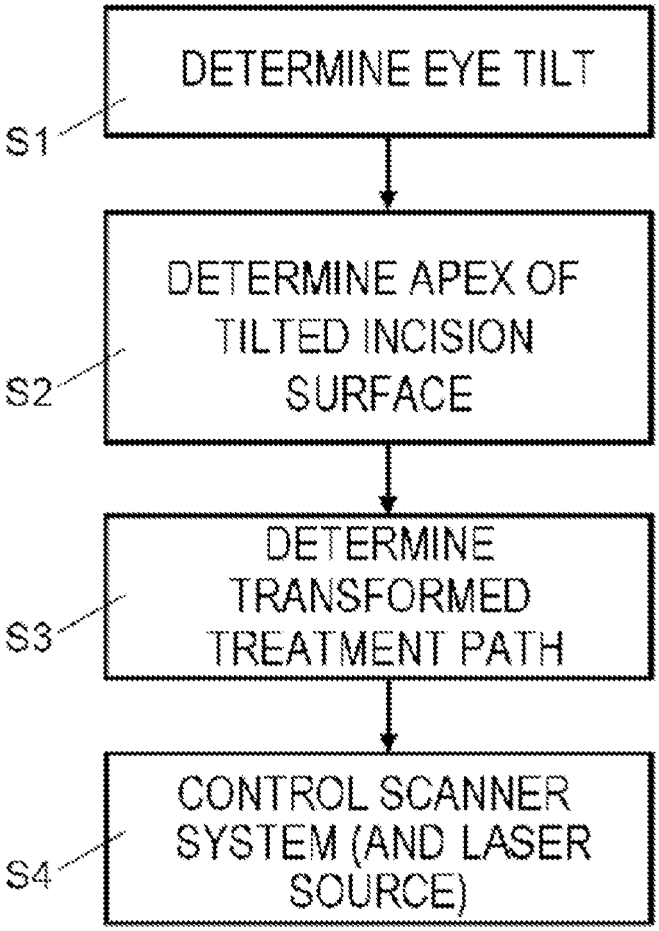
FIG. 12 shows a flowchart, which illustrates a possible sequence of steps for determining an apex of a tilted incision surface and a correspondingly transformed treatment path in the event of a tilt of the eye with respect to the central axis of the patient interface.

In the following sections, with reference to FIG. 12, steps will be described which are carried out by the circuit 2 in order to adapt treatment paths t for the generation of incision surfaces C, C' in the eye tissue 60 when the eye 6 is tilted with respect to the central axis m of the patient interface 52.

In step S1, the circuit 2 receives the reference structures and/or reference markings in or on the eye tissue 60 currently registered by the measuring device 7 and determines any tilt of the eye 6 in relation to the central axis m of the patient interface 52. To this end, the circuit 2 determines displacements and/or rotations of the currently registered reference structures and/or reference markings in relation to the place and orientation of stored reference structures and/or reference markings which have been registered in a previously carried out preparatory step for the eye 6 in question with an untilted alignment of the eye 6 in relation to the central axis m of the patient interface 52 or a reference system. As an alternative, the tilt of the eye 6 in relation to the central axis m of the patient interface 52 (without a measuring device) is determined by the user, who for example carries out a displacement movement in the docked state.

In the event of a tilt of the eye 6 with respect to the central axis m of the patient interface 52, the circuit 2 determines in step S2, on the basis of the stored control data for the treatment path t of the incision surface C to be incised in the eye tissue 60, the apex S' of a tilted incision surface C'. The tilted incision surface C' is defined by a co-tilt of the incision surface C, which corresponds to the tilt of the eye 6 determined in step S1. In other words, the tilted incision surface C' may be incised in the tilted eye 6' in order to incise the incision surface C, defined in the untilted eye 6 by the stored control data, in the eye tissue 60. The determination of the apex S' of the tilted incision surface C' is carried out by determining the highest point of the tilted incision surface C' in respect of the direction of the projection axis p by using and according to the tilt of the eye 6 determined in step S1. Depending on the surface curvature of the incision surface C, or of the tilted incision surface C', in respect of the surface curvature of the curving of the patient interface 52 (or of the eye curvature of the eye 6 adapted to by this curving), the apex S' of the tilted incision surface C' is displaced in relation to the apex S of the untilted incision surface C, as may be seen in the example of FIG. 7. If the incision surface C, or the tilted incision surface C', and the eye 6 have equidistant surfaces, the apex S' of the tilted incision surface C' and the apex S of the untilted incision surface C are at the same place, that is to say in the event of equidistant surfaces of the eye 6 and the incision surface C, the tilt of the eye 6 with the co-tilted incision surface C' causes no displacement of the apex (S=S').

Figure 10:
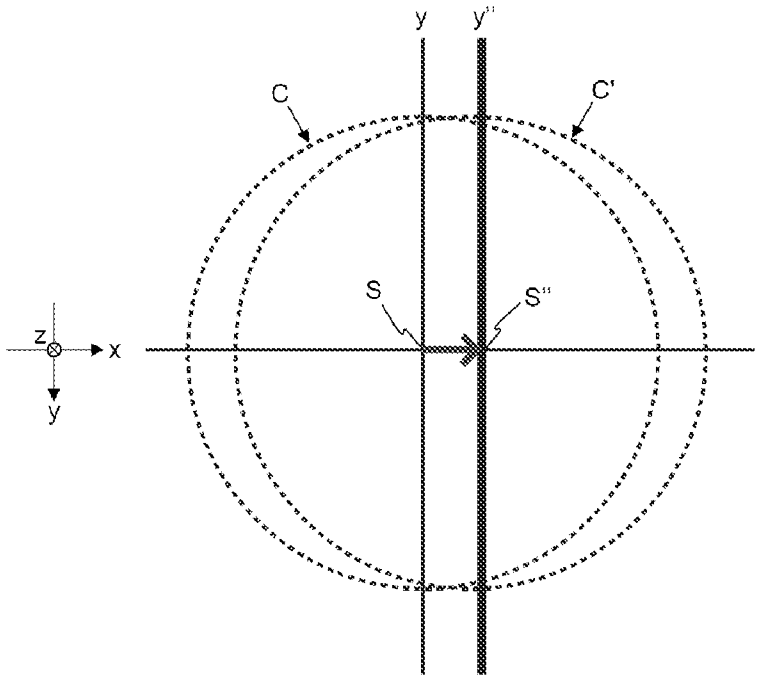
FIG. 10 shows a schematic plan view of a contour of an incision surface, or of a treatment path provided therefor, as well as the contour of the incision surface, or of the treatment path, in the event of a tilt of the eye with respect to the central axis of the patient interface.

FIG. 10 illustrates the untilted incision surface C and the tilted incision surface C' in plan view. As may be seen in FIG. 10, in the case of the tilted incision surface C' the transverse axis y" is displaced in relation to the transverse axis y of the incision surface C in the untilted eye 6. In this case, the apex S of the untilted incision surface S is displaced with respect to the tilted apex S". This tilted apex S" generally does not, however, correspond to the apex S' of the tilted incision surface C'. Depending on the surface curvature of the incision surface C, or of the tilted incision surface C', the apex S' of the tilted incision surface C' lies at the same position as the apex S of the untilted incision surface C (S'=S), at the position of the tilted apex S" (S'=S") or at a position which lies between these two points (S'=[S . . . S"]).

In step S3, the circuit 2 determines a transformed treatment path t' for incising the tilted incision surface C'. FIGS. 7, 8, 9 and 11 show examples of transformed treatment paths t' for incising the tilted incision surface C'. As can be seen in the examples of FIGS. 7, 8, 9 and 11, the transformed treatment path t' is respectively curved and extends around the apex S' of the tilted incision surface C'. The circuit 2 is configured to carry out the transformation, or the generation of the transformed treatment paths t' for incising the tilted incision surface C', while taking into account the dynamics of the scanner system 4 (in particular the scan speed and the feed speed of the scanner system 4), so that the focusing optics 51 can traverse along transformed treatment paths t' without exceeding the maximum focus adjustment speed of the focusing optics 51.

Like the original treatment path t for incising the untilted incision surface C, the treatment path t' transformed by the circuit 2 for incising the tilted incision surface C' can be scanned by the scanner system 4 with the pulsed laser beam L in the x/y treatment plane extending normal to the projection axis p with the scan speed which is higher than the focus adjustment speed of the focusing optics 51, and has height changes in the direction of the projection axis p which the focusing optics 51 can traverse by continual and preferably continuous adjustment of the treatment height (focal depth of the pulsed laser beam L) in the direction of the projection axis p with the focus adjustment speed. Depending on the treatment variant, the treatment height along the transformed treatment path t' may be set by the focusing optics 51 with a continually and continuously increasing or a continually and continuously decreasing treatment height component synchronously with the scanner system 4, or with the scanning, for example in order to scan the treatment points along the transformed treatment path t', by the scanner system 4. In an embodiment, the circuit 2 determines the transformed treatment path t' for incising the tilted incision surface C' with a treatment height component alternately increasing and decreasing in the direction of the projection axis p. In an embodiment, the circuit 2 determines individual path sections of the transformed treatment path t' with a treatment height component alternately increasing and decreasing in the direction of the treatment axis p and/or with an invariant (constant) treatment height.

The transformed treatment path t' comprises one or more mutually separated or connected transformed path sections. The transformed treatment path t' determines treatment points on the tilted incision surface C' for incising the tilted incision surface C'. The circuit 2 determines the transformed treatment path t' on the basis of the original treatment path t defined by the stored control data by one or more of the following transformation steps: distorting one or more regions or the entire original treatment path t by stretching one or more regions or the entire original treatment path t or by compressing one or more regions or the entire original treatment path t, and/or interrupting one or more regions of the entire original treatment path t or of the transformed treatment path t'.

Figure 8:
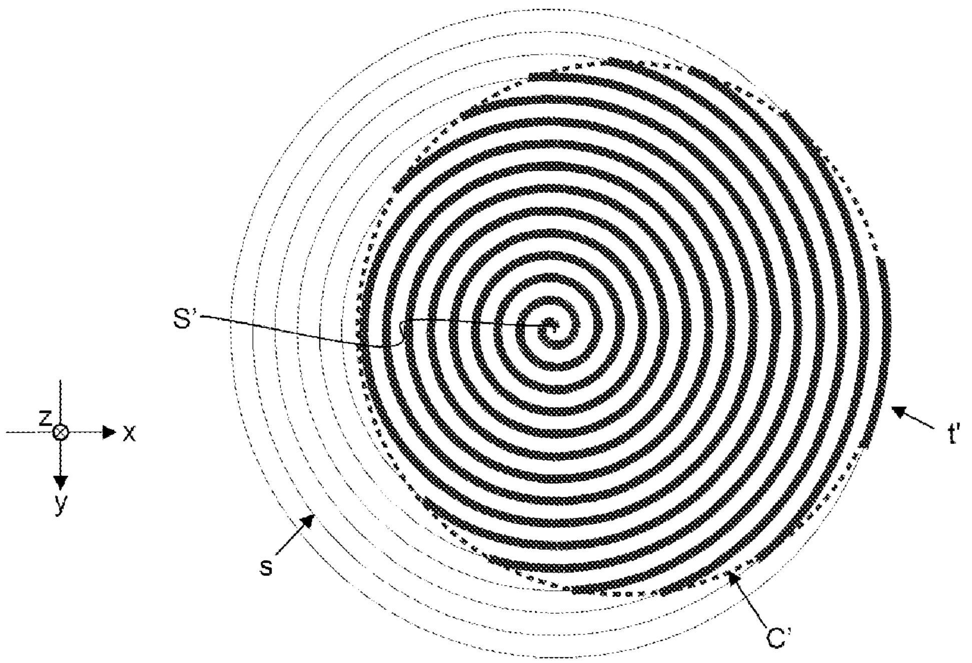
FIG. 8 shows a schematic plan view of a curved treatment path, extending around an apex of a tilted incision surface, with interruptions for incising an incision surface in an eye tissue region, which is tilted with respect to the central axis of the patient interface.
Figure 9:
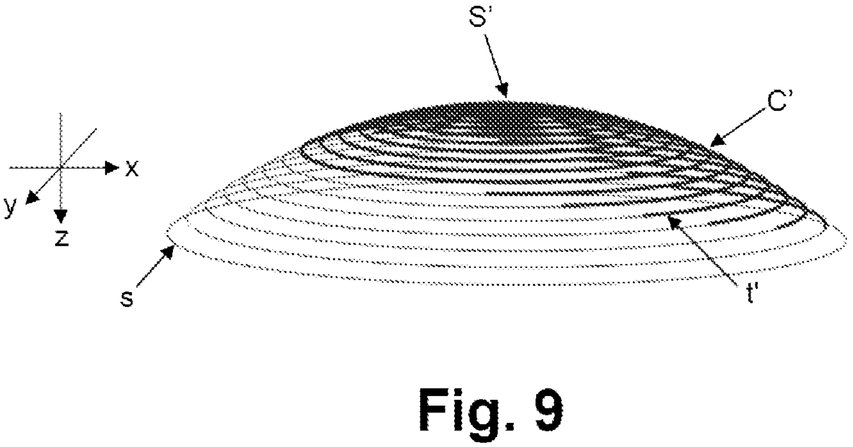
FIG. 9 shows a schematic cross-sectional view of a curved treatment path, extending around an apex of a tilted incision surface, with interruptions for incising an incision surface in an eye tissue region, which is tilted with respect to the central axis of the patient interface.

The transformed treatment path t' in the example of FIG. 7 is generated by a plurality of transformation steps from the treatment path t of FIG. 6 for incising the untilted incision surface C. FIG. 8 illustrates in plan view the transformed treatment path t' of FIG. 7 for incising the tilted incision surface C'. As may be seen in FIG. 8, the transformed treatment path t' extends helically around the (displaced) apex S' of the tilted incision surface C'. The path sections marked in bold represent the treatment path t' scanned by the pulsed laser beam L for incising the tilted incision surface. The regions not marked in bold on the helical path s correspond to interruptions, which are not on the tilted incision surface C' and are not treated by the pulsed laser beam L. FIG. 9 illustrates the transformed treatment path t' of FIGS. 7 and 8 in a schematic three-dimensional view. As may be seen from FIGS. 6, 7, and 8, the transformation is optionally carried out by displacing the original treatment path t from the apex S of the untilted incision surface C to the displaced apex S' of the tilted incision surface C', and on the other hand by introducing additional paths, for example at deeper treatment depth in the direction of the projection axis p in cases with an apex S, S' placed higher in respect of this (as shown in the examples of FIGS. 7 and 9) or at higher treatment depths in the direction of the projection axis p in cases with an apex S, S' placed lower in respect of this, and interruptions on the helical path s.

Figure 11:
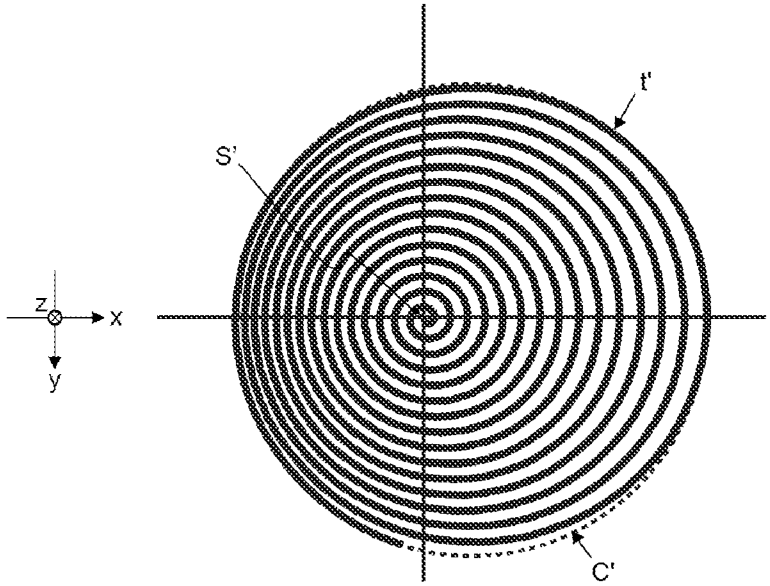
FIG. 11 shows a schematic plan view of a distorted and curved treatment path, extending around an apex of a tilted incision surface, for incising an incision surface in an eye tissue region, which is tilted with respect to the central axis of the patient interface.

The transformed treatment path t' in the example of FIG. 11 is generated by a distortion transformation (compression and/or stretching) from the treatment path t for incising an untilted incision surface C. In the example of FIG. 11, the transformed treatment path t' is transformed only by distortion (compression and/or stretching) of the treatment path t for incising the untilted incision surface C into the transformed treatment path t' for incising at least a subregion of the tilted incision surface C'. Further supplementary subregions of the tilted incision surface C' are optionally treated with additional transformed treatment paths t', which comprises interruptions.

In step S4, the circuit 2 controls the scanner system 4 so that the pulsed laser beam L is steered onto treatment points F on the transformed treatment path t'. The circuit 2 controls the scanner system 4 so that the pulsed laser beam L scans the transformed treatment path t' and incises the tilted incision surface C'. In the case of interrupted path sections on the transformed treatment path t', the circuit 2 controls the laser source 3 so that the pulsed laser beam L is turned off in interruptions of the transformed treatment path t'. As soon as the adjustment of the focusing optics 51 in the direction of the projection axis p has reached the treatment height and the scanner system 4 has reached the x/y position (for example in relation to the projection axis p) of the first treatment point after the interruption of the transformed treatment path t', the circuit 2 controls the laser source 3 so that the pulsed laser beam L is again activated, or switched on, and focused onto the relevant treatment point F on the transformed treatment path t'. In embodiments, or treatment variants, in which subsections of the treatment path t and/or of the transformed treatment path t' have an invariant (constant) treatment height, the circuit 2 controls the focusing optics 51 so that it leaves the treatment height unchanged on the relevant subsections and then adjusts the treatment height before or during the treatment of the subsequent path section of the treatment path t and/or of the transformed treatment path t'.

What is claimed is:

1. Ophthalmological device for treating eye tissue of an eye, comprising:

a laser source which is configured to generate a pulsed laser beam;

an application head having focussing optics and a patient interface, the focussing optics having a projection axis and being configured to focus the pulsed laser beam in the eye tissue onto a treatment point, and the patient interface having a central axis and being configured to fix the application head on the eye; a scanner system which is configured to steer the pulsed laser beam in the eye tissue onto treatment points on a treatment path; and a circuit which is configured to control the scanner system in order to incise an incision surface, which is symmetrical with respect to the central axis of the patient interface, in the eye tissue, the pulsed laser beam being steered onto treatment points on the incision surface on a first treatment path, and the first treatment path being curved while extending around the projection axis of the focussing optics, wherein the circuit is furthermore configured, in the event of a tilt of the eye with respect to the central axis of the patient interface, to determine an apex of a tilted incision surface, which is determined by a co-tilt of the incision surface corresponding to the tilt of the eye, to determine a transformed second curved treatment path, which extends around the apex and determines treatment points on the tilted incision surface, wherein the transformed second curved treatment path is determined on the basis of the first curved treatment path by carrying out at least one of the following operations: stretching first regions of the first curved treatment path, compressing second regions of the first curved treatment path, or interrupting third regions of the first curved treatment path, and to control the scanner system in such a way that the pulsed laser beam is steered onto treatment points on the transformed second curved treatment path.

2. Ophthalmological device for treating eye tissue of an eye, comprising:

a laser source which is configured to generate a pulsed laser beam;

an application head having focussing optics and a patient interface, the focussing optics having a projection axis and being configured to focus the pulsed laser beam in the eye tissue onto a treatment point, the focussing optics being configured to adjust a treatment height of the treatment points in the direction of the projection axis with a focus adjustment speed, and the patient interface having a central axis and being configured to fix the application head on the eye;

a scanner system which is configured to steer the pulsed laser beam in the eye tissue onto treatment points on a treatment path, the scanner system being further configured to displace treatment points on the treatment path with a scan speed that is higher than the focus adjustment speed; and a circuit which is configured to control the scanner system in order to incise an incision surface, which is symmetrical with respect to the central axis of the patient interface, in the eye tissue, the pulsed laser beam being steered onto treatment points on the incision surface on a first treatment path, and the first treatment path being curved while extending around the projection axis of the focussing optics, wherein the circuit is furthermore configured, in the event of a tilt of the eye with respect to the central axis of the patient interface, to determine an apex of a tilted incision surface, which is determined by a co-tilt of the incision surface corresponding to the tilt of the eye, to determine a transformed second curved treatment path, which extends around the apex and determines treatment points on the tilted incision surface, and wherein the circuit is configured to determine the transformed second curved treatment path with height changes in the direction of the projection axis which are adjustable during a movement of treatment points with the scan speed without exceeding the focus adjustment speed of the focussing optics, and to control the scanner system in such a way that the pulsed laser beam is steered onto treatment points on the transformed second curved treatment path.

3. Ophthalmological device according to claim 2, wherein the first treatment path has a continual height change component in the direction of the projection axis, and in that the circuit is configured to determine the transformed second curved treatment path with a treatment height component increasing continually or decreasing continually in the direction of the projection axis.

4. Ophthalmological device according to claim 1, wherein the first treatment path has a continual height change component in the direction of the projection axis, and in that the circuit is configured to determine the transformed second curved treatment path with a treatment height component increasing continually or decreasing continually in the direction of the projection axis.

5. Ophthalmological device according to claim 4, wherein the first treatment path has a continual height change component in the direction of the projection axis, and in that the circuit is configured to determine subsections of the transformed second curved treatment path with a path section treatment height that is respectively constant in the direction of the projection axis, and to prevent generation of the pulsed laser beam by the laser source while the focussing optics are adjusting the path section treatment height of two subsections, which two subsections are adjacent in the direction of the projection axis, of the transformed second curved treatment path.

6. Ophthalmological device according to claim 1, wherein the first treatment path has a continual height change component in the direction of the projection axis, and in that the circuit is configured to determine subsections of the transformed second curved treatment path with a path section treatment height that is respectively constant in the direction of the projection axis, and to prevent generation of the pulsed laser beam by the laser source while the focussing optics are adjusting the path section treatment height of two subsections, which two subsections are adjacent in the direction of the projection axis, of the transformed second curved treatment path.

7. Ophthalmological device according to claim 6, wherein subsections of the first treatment path respectively have a path section treatment height that is constant in the direction of the projection axis, and in that the circuit is configured to determine the transformed second curved treatment path with a treatment height component increasing continually or decreasing continually in the direction of the projection axis.

8. Ophthalmological device according to claim 1, wherein subsections of the first treatment path respectively have a path section treatment height that is constant in the direction of the projection axis, and in that the circuit is configured to determine the transformed second curved treatment path with a treatment height component increasing continually or decreasing continually in the direction of the projection axis.

9. Ophthalmological device according to claim 1, wherein subsections of the first treatment path respectively have a path section treatment height that is constant in the direction of the projection axis, and in that the circuit is configured to determine subsections of the transformed second curved treatment path with a path section treatment height that is respectively constant in the direction of the projection axis, and to prevent generation of the pulsed laser beam by the laser source while the focussing optics are adjusting the path section treatment height of two subsections, adjacent in the direction of the projection axis, of the transformed second curved treatment path.

10. Ophthalmological device according to claim 1, wherein the circuit is configured to determine the transformed second curved treatment path with a treatment height component alternately increasing and decreasing in the direction of the projection axis.

11. Ophthalmological device according to claim 1, wherein the first treatment path comprises path sections having at least one of the following shapes: a circular path section, an elliptical path section, a parabolic path section, a hyperbolic path section, a helical path section, or a spline path section.

12. Ophthalmological device according to claim 1, wherein the circuit is configured to control the scanner system in order to incise a lenticule, which lenticule is formed by two incision surfaces and is symmetrical with respect to the central axis of the patient interface in the eye tissue, and in the event of a tilt of the eye with respect to the central axis of the patient interface, to determine an apex of a tilted lenticule which is determined by a co-tilt of the lenticule corresponding to the tilt of the eye, to determine transformed third curved treatment paths which extend around the apex and determine treatment points on the incision surfaces of the tilted lenticule, and to control the scanner system in such a way that the pulsed laser beam is steered onto treatment points on the transformed third curved treatment paths.

13. Ophthalmological device according to claim 1, wherein the patient interface comprises a curved internal space, which is symmetrical with respect to the central axis, for receiving a corneal region of the eye.

14. Ophthalmological device according to claim 1, wherein the scanner system comprises a first scan device, which is configured to steer the pulsed laser beam in the eye tissue with a feed speed along a feed line on the treatment path, and in that the scanner system comprises a second scan device, which is configured to steer the pulsed laser beam in the eye tissue with a scan speed, which is higher than the feed speed, along a scan line extending transversely with respect to the feed line on the treatment path.

15. Ophthalmological device according to claim 1, further comprising one or more suction elements, which are configured to fix the patient interface on the eye.

16. Ophthalmological device for treating eye tissue of an eye, comprising:

a laser source which is configured to generate a pulsed laser beam;

an application head having focussing optics and a patient interface, the focussing optics having a projection axis and being configured to focus the pulsed laser beam in the eye tissue onto a treatment point, and the patient interface having a central axis and being configured to fix the application head on the eye; a scanner system which is configured to steer the pulsed laser beam in the eye tissue onto treatment points on a treatment path, wherein the patient interface comprises a planar internal space, which is symmetrical with respect to the central axis, for receiving a corneal region of the eye; and a circuit which is configured to control the scanner system in order to incise an incision surface, which is symmetrical with respect to the central axis of the patient interface, in the eye tissue, the pulsed laser beam being steered onto treatment points on the incision surface on a first treatment path, and the first treatment path being curved while extending around the projection axis of the focussing optics, wherein the circuit is furthermore configured, in the event of a tilt of the eye with respect to the central axis of the patient interface, to determine an apex of a tilted incision surface, which is determined by a co-tilt of the incision surface corresponding to the tilt of the eye, to determine a transformed second curved treatment path, which extends around the apex and determines treatment points on the tilted incision surface, and to control the scanner system in such a way that the pulsed laser beam is steered onto treatment points on the transformed second curved treatment path.

17. Ophthalmological device for treating eye tissue of an eye, comprising:

a laser source which is configured to generate a pulsed laser beam;

an application head having focussing optics and a patient interface, the focussing optics having a projection axis and being configured to focus the pulsed laser beam in the eye tissue onto a treatment point, and the patient interface having a central axis and being configured to fix the application head on the eye;

a scanner system which is configured to steer the pulsed laser beam in the eye tissue onto treatment points on a treatment path;

a measuring device which is configured to register reference structures and/or reference markings in or on the eye tissue, and a circuit which is configured to control the scanner system in order to incise an incision surface, which is symmetrical with respect to the central axis of the patient interface, in the eye tissue, the pulsed laser beam being steered onto treatment points on the incision surface on a first treatment path, and the first treatment path being curved while extending around the projection axis of the focussing optics, wherein the circuit is configured to determine a tilt of the eye with respect to the central axis of the patient interface on the basis of the reference structures and/or reference markings registered by the measuring device, wherein the circuit is furthermore configured, in the event of a tilt of the eye with respect to the central axis of the patient interface, to determine an apex of a tilted incision surface, which is determined by a co-tilt of the incision surface corresponding to the tilt of the eye, to determine a transformed second curved treatment path, which extends around the apex and determines treatment points on the tilted incision surface, and to control the scanner system in such a way that the pulsed laser beam is steered onto treatment points on the transformed second curved treatment path.

* * * * *